United States Patent [19]

Franz et al.

[11] Patent Number: 6,013,604
[45] Date of Patent: Jan. 11, 2000

[54] SYNERGISTIC HERBICIDAL COMBINATION

[75] Inventors: Richard Lynn Franz, Richmond; Khosro Khodayari, Walnut Creek, both of Calif.

[73] Assignee: Zeneca Limited, London, United Kingdom

[21] Appl. No.: 09/288,737

[22] Filed: Apr. 7, 1999

Related U.S. Application Data

[63] Continuation-in-part of application No. 09/056,760, Apr. 7, 1998, abandoned.

[51] Int. Cl.$^7$ .......................... A01N 43/00; A01N 43/48; A01N 43/647

[52] U.S. Cl. .......................... 504/129; 504/139; 504/166; 504/169

[58] Field of Search .................... 504/139, 169, 504/129, 166

[56] References Cited

PUBLICATIONS

Tomlyn, The Pesticide Manual Incorporating the Agrochemicals Handbook, 10$^{th}$ Ed. (1995) pp. 421, 422, 206 + 207.

*Primary Examiner*—Allen J. Robinson
*Attorney, Agent, or Firm*—Liza D. Hohenschutz

[57] ABSTRACT

Control of weeds in a rice crop is obtained by applying to the crop, the weeds, or the locus of either or both, a herbicidal composition containing molinate and carfentrazone-ethyl in a weight ratio of from about 60:1 to about 6:1.

12 Claims, No Drawings

5,013,604

SYNERGISTIC HERBICIDAL COMBINATION

This is a continuation-in-part of application Ser. No. 09/056,760 filed on Apr. 7, 1998 now abandoned.

BACKGROUND OF THE INVENTION

This invention pertains to synergistic herbicidal combinations, particularly such combinations for use in controlling weeds in a rice crop.

Molinate (S-ethyl hexahydro-1H-azepine-1-carbothioate) is a thiocarbamate herbicide which has been used to control weeds in rice crops for a number of years, and is generally sold under products bearing the trademark ORDRAM®. In different formulations and strengths, molinate is applied pre-plant, pre-flood or post-flood to control a wide range of weeds in rice crops, and is generally applied at rates ranging from about 500 to about 11,000 g/ha. However, as with many herbicides, it would be desirable to be able to achieve weed control while using a lower application rate of molinate. This could also result in less impact upon the environment and/or upon workers handling the product. Molinate is also sold mixed with propanil (N-3,4-(dichlorophenyl) propanamide) in a product bearing the trademark ARROSOLO®.

Carfentrazone-ethyl, or ethyl 2-chloro-3-[2-chloro-5-(4-difluoromethyl-4,5-dihydro-3-methyl -5-oxo-1 H-1,2,4-triazol-1-yl)phenyl] propionate (also known as F8426) is known as a selective herbicide for control of broadleaf weeds in cereal crops and is described in Van Saun et al., Proc. Brit. Crop Protection Conf. Weeds, p-19 (1993). Its preparation is described in the paper by Theodoridis et al., Synthesis and Chemistry of Agrochemicals IV (American Chemical Society, 1995, Don R. Baker et al., editors), p. 90.

SUMMARY OF THE INVENTION

This invention comprises a herbicidal composition as well as a method of controlling weeds in rice crops.

In one aspect, this invention relates to a synergistic herbicidal composition comprising molinate and carfentrazone-ethyl.

In a second aspect, it comprises a herbicidal composition comprising molinate and carfentrazone-ethyl in a weight ratio of from about 60:1 to about 6:1, respectively.

In another aspect, this invention comprises a method of controlling weeds in a rice crop comprising applying to said crop, said weeds or the locus of either or both, a synergistic combination comprising molinate and carfentrazone-ethyl, particularly in a weight ratio of from about 60:1 to about 6:1, respectively.

It has now been found that, surprisingly, combining of a lesser amount of the herbicide carfentrazone-ethyl with molinate can produce a synergistic effect such that equivalent weed control can be obtained with a lesser amount and/or application rate of molinate.

DETAILED DESCRIPTION OF THE INVENTION

The invention involves the use of the combination of the herbicides molinate and carfentrazone-ethyl to control weeds in a rice crop. The combination, within the scope of this invention, demonstrates synergistic effects, that is, effects that would have been unexpected from the performance of the two herbicides individually against the same weeds under similar circumstances.

According to the invention, weeds are controlled in the presence of a rice crop by treating the crop, the weeds, or the locus of either or both, with a herbicidally effective amount of a synergistic combination of the herbicides molinate and carfentrazone-ethyl. In general, we have found that synergy is demonstrated when the combination includes these two herbicides in a weight ratio respectively, of from about 60:1 to about 6:1, preferably, from about 20:1 to about 6:1. However, our discovery is that of synergism between molinate and carfentrazone-ethyl, and is not necessarily limited to combinations of these herbicides within these weight ratios, as synergy may exist at others.

This combination produces synergistic or unexpected control of weeds in rice when applied at various times, and to rice planted in different ways. To control the weeds, the combination may be applied prior to planting, after planting but prior to flooding (pre-flood, post-emergence) or after emergence of the rice and flooding (post-flood, post-emergence) and may be applied to either direct seeded or transplanted rice.

To be used in combination, it is not necessary that the two herbicides molinate and carfentrazone-ethyl, be applied in a physically combined form, or even at the same time. The combination effect results so long as the two herbicides are present at the same time in the rice crop, regardless of when they were applied. Thus, for instance, a physical combination of the two herbicides could be applied, or one could be applied earlier than the other. For instance, one of the two herbicides could be applied even prior to planting the rice in a controlled release formulation such as a microencapsulated formulation, and the other applied subsequently in a conventional liquid or solid formulation, so long as the earlier-applied herbicide is still present in the soil when the second is applied, and so long as the weight ratio of available herbicides falls within that disclosed and claimed herein.

Either herbicide could thus be applied in liquid or solid form, or a combination product containing both herbicides could be produced, again, in either liquid or solid form. Typical liquid formulations include emulsions, suspensions (including suspensions containing microcapsules), solutions, emulsifiable concentrates, and flowables. Solid products include forms such as granules, wettable powders, water-dispersible solid products (including water-dispersible granules containing microencapsulated pesticides) or dusts. Both types of compositions will generally contain, in addition to the active herbicide, other ingredients such as solvents, wetting agents, suspending agents, anti-caking agents, dispersing agents, emulsifiers, antifreeze agents, antifoam agents, and other additives.

Either herbicide, or both, may be utilized in one of a number of known forms of controlled release compositions. Such compositions provide relatively slow or controlled release of the active ingredient into the environment and include, for example, encapsulations, microencapsulations, and various forms of controlled release granules.

Combination products or compositions according to this invention, may contain the two herbicides in numerous different physical forms. In some cases, a combination product may be produced by simply physically mixing ("tank-mixing") commercially available products containing the active herbicides, for example, two emulsifiable concentrates containing the herbicides, so long as all the ingredients of the two products are relatively compatible. Alternatively, a package may be manufactured and sold which contains overall the two herbicides in separate containers, but packaged together, commonly termed a "twin-pack". A twin-pack is particularly suitable for the herbicidal compositions herein, since the amount of molinate is substantially greater than that of carfentrazone-ethyl, so that an overall product package can be produced containing a relatively large container of a molinate-containing herbicide product together with a relatively small container of a carfentrazone-ethyl containing herbicidal product.

Alternatively, previously prepared compositions ("premixes") containing the two herbicides can be produced. Since both molinate and carfentrazone-ethyl are liquids under normal conditions, liquid premixes would tend to be preferred. Typical liquid compositions would include an emulsifiable concentrate containing both herbicides, and a two-phase emulsion (or microemulsion) with one herbicide in each phase.

However, a similar solid product containing both herbicides could likewise be produced, for instance, as impregnated granules. Similarly, other solid formulations such as wettable powders or dusts could be prepared.

Again similarly, using appropriate ingredients and conditions, it would be possible to prepare microencapsulated products in which one or both herbicides are contained within a microcapsule and said microencapsulated products could be sold in either liquid form (i.e., capsule suspensions) or solid form (i.e., water-dispersible granules produced by drying of microcapsule suspensions). One type of liquid form would be a microcapsule suspension in which one of the herbicides is contained within the capsules while the other is present in a nonencapsulated form, in the continuous liquid phase. Another type would be a suspension containing molinate and carfentrazone-ethyl separately encapsulated. The types of formulations or compositions which may contain these two herbicides is not limited by those enumerated herein, as other types of formulations would likely be envisaged by those skilled in the art.

Additionally, other biocidally active ingredients or compositions may be combined with the herbicidal compositions of the present invention and used in the methods of the present invention. In addition to molinate and carfentrazone-ethyl, the herbicidal compositions of the present invention can also contain insecticides, fungicides, bactericides, acaracides, nematicides or other herbicides, especially herbicides known to be useful for controlling weeds in a rice crop. For example, in addition to molinate and carfentrazone-ethyl, the herbicidal compositions of the present invention can also contain propanil. Propanil is commercially available, and can also be obtained mixed with molinate in a product sold under the trademark ARROSOLO® which can be used in the herbicidal compositions of the invention. In the ARROSOLO product, molinate and propanil are present in a weight ratio of 1:1. As discussed above in relation to molinate and carfentrazone-ethyl, it is not necessary that an additional biocidally active ingredient or composition be applied in a form physically combined with molinate or carfentrazone-ethyl, or even applied at the same time.

The control of weeds by the combination of carfentrazone-ethyl and molinate is illustrated by the following examples:

EXAMPLE 1

This example simulates application of the combination of molinate and carfentrazone-ethyl in a direct seeded rice culture under conditions typical of the Americas. Combinations of molinate and carfentrazone-ethyl in the indicated amounts were applied in the greenhouse at the application rates shown in Table 1 (in terms of grams per hectare of the herbicide or herbicides) to flats containing rice (*Oryza sativa*, variety Katy) and the weeds barnyardgrass (*Echinochloa crusgalli*, ECHCG), morningglory (*Ipomoea wrightii*) (IPOWR) and rice flatsedge (*Cyperus iria*, CYPIR) at the pre-flood postemergence stage, and at the 2-leaf growth stage of the barnyardgrass. The weeds had been grown separately to the 2-leaf stage, then transplanted to the rice flats. Results of these tests are shown in Table 1, below, in terms of percent control or injury as compared to an untreated check flat 30 days after treatment. A rating of 100% indicates complete control; of 0% indicates no effect.

Synergistic herbicidal activity can be calculated according to the Colby method (S. R. Colby, "Calculating Synergistic and Antagonistic Response Of Herbicide Combinations", Weeds, 15(1): 20–23, 1967). The Colby method represents a direct approach to measuring the synergistic activity of two herbicides. According to the Colby method, $E=X+Y-(XY/100)$, wherein E is the expected percent weed control for a combination of a first herbicide H1 and a second herbicide H2 at an application rate of p+q g/ha; X is the percent weed control observed for H1 at an application rate p g/ha; and Y is the percent weed control observed for H2 at an application rate q g/ha.

Synergistic herbicidal activity calculated in accordance with the Colby shows that synergistic activity is found with *Echinolochia crusgalli* (ECHCG).

TABLE 1

| Compound(s) | Rate of molinate (g/ha) | Rate of carfentrazone-ethyl (g/ha) | Rice Injury % | ECHCG, % control | IPOWR, % control | CYPIR % control |
|---|---|---|---|---|---|---|
| carfentrazone-ethyl | — | 25 | 0 | 0 | 100 | 41 |
| carfentrazone-ethyl | — | 50 | 0 | 0 | 100 | 66 |
| carfentrazone-ethyl | — | 75 | 0 | 0 | 100 | 68 |
| molinate | 500 | — | 0 | 0 | 0 | 81 |
| molinate & carfentrazone-ethyl | 500 | 25 | 0 | 54 | 75 | 75 |
| molinate & carfentrazone-ethyl | 500 | 50 | 0 | 68 | 90 | 73 |
| molinate & carfentrazone-ethyl | 500 | 75 | 0 | 88 | 88 | 74 |

TABLE 1-continued

| Compound(s) | Rate of molinate (g/ha) | Rate of carfentrazone-ethyl (g/ha) | Rice Injury % | ECHCG, % control | IPOWR, % control | CYPIR, % control |
|---|---|---|---|---|---|---|
| carfentrazone-ethyl | | | | | | |
| molinate | 750 | — | 0 | 0 | 0 | 65 |
| molinate & carfentrazone-ethyl | 750 | 25 | 0 | 21 | 100 | 74 |
| molinate & carfentrazone-ethyl | 750 | 50 | 0 | 61 | 100 | 76 |
| molinate & carfentrazone-ethyl | 750 | 75 | 0 | 100 | 100 | 69 |
| molinate | 1000 | — | 0 | 6 | 0 | 75 |
| molinate & carfentrazone-ethyl | 1000 | 25 | 0 | 55 | 100 | 78 |
| molinate & carfentrazone-ethyl | 1000 | 50 | 0 | 83 | 100 | 83 |
| molinate & carfentrazone-ethyl | 1000 | 75 | 0 | 94 | 93 | 75 |
| molinate | 1500 | — | 0 | 39 | 0 | 88 |
| molinate & carfentrazone-ethyl | 1500 | 25 | 0 | 64 | 100 | 84 |
| molinate & carfentrazone-ethyl | 1500 | 50 | 0 | 76 | 100 | 82 |
| molinate & carfentrazone-ethyl | 1500 | 75 | 0 | 94 | 100 | 80 |

EXAMPLE 2

This example demonstrates preflood postemergence application of molinate and carfentrazone-ethyl to a direct seeded rice culture under conditions typical of the Southern United States. Dry rice seed (Kaybonnet variety) was planted 1 cm deep, then watered and grown to the 3-leaf stage. Weeds used were ECHCG, IPOWR and CYPIR, as before. Weeds were grown separately to the 2 leaf growth stage and added to the tubs. Herbicide application was by spraying or broadcasting of chemical. Tubs were flooded 1 week or more after application. The results of these are shown in the following Table 2. Ratings were taken 28 days after application.

Synergistic herbicidal activity was calculated using the Colby method set out in Example 1. Synergistic herbicidal activity is found with *Echinolochia crusgalli* (ECHCG) and *Ipomoea wrightii* (IPOWR).

TABLE 2

| Compound(s) | Rate of molinate (g/ha) | Rate of carfentrazone-ethyl (g/ha) | Rice Injury % | ECHCG, % control | IPOWR, % control | CYPIR, % control |
|---|---|---|---|---|---|---|
| carfentrazone-ethyl | — | 25 | 0 | 0 | 13 | 56 |
| carfentrazone-ethyl | — | 50 | 0 | 0 | 50 | 83 |
| carfentrazone-ethyl | — | 75 | 0 | 5 | 59 | 94 |
| molinate | 500 | — | 0 | 28 | 0 | 23 |
| molinate & carfentrazone-ethyl | 500 | 25 | 0 | 21 | 49 | 59 |
| molinate & carfentrazone-ethyl | 500 | 50 | 0 | 43 | 53 | 77 |
| molinate & carfentrazone-ethyl | 500 | 75 | 0 | 54 | 60 | 100 |
| molinate | 750 | — | 0 | 33 | 28 | 38 |
| molinate & carfentrazone-ethyl | 750 | 25 | 0 | 55 | 38 | 60 |
| molinate & carfentrazone-ethyl | 750 | 50 | 0 | 85 | 55 | 87 |
| molinate & carfentrazone-ethyl | 750 | 75 | 0 | 80 | 65 | 98 |
| molinate | 1000 | — | 0 | 40 | 0 | 44 |
| molinate & carfentrazone-ethyl | 1000 | 25 | 0 | 60 | 40 | 49 |
| molinate & carfentrazone-ethyl | 1000 | 50 | 1 | 43 | 53 | 69 |
| molinate & carfentrazone-ethyl | 1000 | 75 | 1 | 76 | 40 | 100 |
| molinate | 1500 | — | 0 | 55 | 0 | 38 |
| molinate & carfentrazone-ethyl | 1500 | 25 | 1 | 70 | 46 | 80 |

TABLE 2-continued

| Compound(s) | Rate of molinate (g/ha) | Rate of carfentrazone-ethyl (g/ha) | Rice Injury % | ECHCG, % control | IPOWR, % control | CYPIR, % control |
|---|---|---|---|---|---|---|
| molinate & carfentrazone-ethyl | 1500 | 50 | 0 | 81 | 51 | 99 |
| molinate & carfentrazone-ethyl | 1500 | 75 | 0 | 100 | 44 | 100 |

EXAMPLE 3

This example involved tests conducted using postflood, postemergence application (at the 2-leaf stage of barnyardgrass) in transplanted rice variety Koshihikari. Rice was grown to the 2–4 leaf stage away separately from the trial tubs. The soil in the tub was puddled until a blend was achieved. The rice plants were then transplanted into this blend. Weeds used were ECHCG, smallflower flatsedge (*Cyperus difformis*, CYPDI), dwarf arrowhead (*Sagittaria pygmae*, SAGPY) and monochoria (*Monochoria vaginalis*, MOOVA). Weeds (2 leaf stage) were either grown separately and transplanted in or were grown in the tub on the blended soil. Herbicide application typically took place by injection or broadcasting of chemical after flooding. Ratings were taken 29 days after application and represent the average of four plots. The results are shown in the following Table 3.

Synergistic herbicidal activity was calculated using the Colby method set out in Example 1. Synergistic herbicidal activity is found with *Echinolochia crusgalli* (ECHCG), *Monochoria vaginalis* (MOOVA), *Sagittaria pygmae* (SAGPY) and *Cyperus difformis* (CYPDI).

What is claimed is:

1. A herbicidal composition comprising synergistic herbicidally effective amount of molinate and carfentrazone-ethyl in a weight ratio of from about 60:1 to about 6:1, respectively.

2. A herbicidal composition according to claim 1 in which the weight ratio is from about 20.1 to about 6:1.

3. A liquid herbicidal composition according to claim 1.

4. A solid herbicidal composition according to claim 1.

5. A controlled release herbicidal composition according to claim 1.

6. A herbicidal composition according to claim 5 in which at least one of molinate and carfentrazone-ethyl is contained in microcapsules.

7. A method of controlling weeds in the presence of a rice crop comprising applying to said crop, said weeds, or the locus of said crop and/or said weeds, a herbicidally effective amount of a composition according to claim 1.

8. A method of controlling weeds in the presence of a rice crop comprising applying to said crop, said weeds, or the locus of said crop and/or said weeds, a herbicidally effective amount of a composition according to claim 2.

TABLE 3

| Compound(s) | Rate of molinate (g/ha) | Rate of carfentrazone-ethyl (g/ha) | Rice Injury % | ECHCG % control | MOOVA % control | SAGPY % control | CYPDI % control |
|---|---|---|---|---|---|---|---|
| carfentrazone-ethyl | — | 12 | 2 | 0 | 80 | 0 | 85 |
| carfentrazone-ethyl | — | 25 | 4 | 0 | 100 | 75 | 100 |
| carfentrazone-ethyl | — | 50 | 5 | 0 | 100 | 90 | 100 |
| molinate | 500 | — | 0 | 46 | 75 | 25 | 100 |
| molinate & carfentrazone-ethyl | 500 | 12 | 2 | 29 | 100 | 35 | 70 |
| molinate & carfentrazone-ethyl | 500 | 25 | 3 | 26 | 100 | 61 | 95 |
| molinate & carfentrazone-ethyl | 500 | 50 | 5 | 49 | 100 | 99 | 100 |
| molinate | 750 | — | 1 | 48 | 40 | 23 | 30 |
| molinate & carfentrazone-ethyl | 750 | 12 | 2 | 38 | 100 | 0 | 84 |
| molinate & carfentrazone-ethyl | 750 | 25 | 2 | 40 | 100 | 90 | 100 |
| molinate & carfentrazone-ethyl | 750 | 50 | 4 | 66 | 100 | 95 | 100 |
| molinate | 1000 | — | 0 | 55 | 43 | 31 | 65 |
| molinate & carfentrazone-ethyl | 1000 | 12 | 3 | 76 | 88 | 33 | 93 |
| molinate & carfentrazone-ethyl | 1000 | 25 | 4 | 63 | 100 | 66 | 96 |
| molinate & carfentrazone-ethyl | 1000 | 50 | 3 | 94 | 100 | 94 | 100 |
| molinate | 1500 | — | 1 | 69 | 45 | 0 | 85' |
| molinate & carfentrazone-ethyl | 1500 | 12 | 2 | 74 | 94 | 36 | 100 |
| molinate & carfentrazone-ethyl | 1500 | 25 | 2 | 88 | 90 | 79 | 98 |
| molinate & carfentrazone-ethyl | 1500 | 50 | 4 | 90 | 100 | 98 | 100 |

9. A method of controlling weeds in the presence of a rice crop comprising applying to said crop, said weeds, or the locus of said crop and/or said weeds, a herbicidally effective amount of a composition according to claim 3.

10. A method of controlling weeds in the presence of a rice crop comprising applying to said crop, said weeds, or the locus of said crop and/or said weeds, a herbicidally effective amount of a composition according to claim 4.

11. A method of controlling weeds in the presence of a rice crop comprising applying to said crop, said weeds, or the locus of said crop and/or said weeds, a herbicidally effective amount of a composition according to claim 5.

12. A method of controlling weeds in the presence of a rice crop comprising applying to said crop, said weeds, or the locus of said crop and/or said weeds, a herbicidally effective amount of a composition according to claim 6.

* * * * *